US011364265B1

(12) United States Patent
Soon-Shiong et al.

(10) Patent No.: US 11,364,265 B1
(45) Date of Patent: Jun. 21, 2022

(54) RECOMBINANT ERIL-15 NK CELLS

(71) Applicants: NantCell, Culver City, CA (US); NantBio, Inc., Culver City, CA (US); NantKwest, Inc., San Diego, CA (US)

(72) Inventors: Patrick Soon-Shiong, Culver City, CA (US); Shahrooz Rabizadeh, Agoura Hills, CA (US); Kayvan Niazi, Culver City, CA (US); Hans G. Klingemann, Culver City, CA (US)

(73) Assignees: NantCell, Inc., Culver City, CA (US); NantBio, Inc., Culver City, CA (US); ImmunityBio, Inc., Culver City, CA (US)

( * ) Notice: Subject to any disclaimer, the term of this patent is extended or adjusted under 35 U.S.C. 154(b) by 0 days.

(21) Appl. No.: 17/438,386

(22) PCT Filed: Feb. 27, 2020

(86) PCT No.: PCT/US2020/019991
§ 371 (c)(1),
(2) Date: Sep. 10, 2021

(87) PCT Pub. No.: WO2020/205100
PCT Pub. Date: Oct. 8, 2020

Related U.S. Application Data

(60) Provisional application No. 62/819,256, filed on Mar. 15, 2019.

(51) Int. Cl.
*A61K 35/17* (2015.01)
*A61P 35/00* (2006.01)
*C12N 5/0783* (2010.01)
*C07K 14/54* (2006.01)

(52) U.S. Cl.
CPC .............. *A61K 35/17* (2013.01); *A61P 35/00* (2018.01); *C07K 14/5443* (2013.01); *C12N 5/0646* (2013.01)

(58) Field of Classification Search
CPC .................................................. A61K 35/17
See application file for complete search history.

(56) References Cited

U.S. PATENT DOCUMENTS

| 9,487,800 B2 | 11/2016 | Schonfeld et al. |
| 2018/0344768 A1 | 12/2018 | O'dwyer et al. |

FOREIGN PATENT DOCUMENTS

| AU | 2013203171 B2 | 9/2016 |
| TW | 202102666 A | 1/2021 |
| WO | 2012/136231 A1 | 10/2012 |
| WO | 2013/040371 A2 | 3/2013 |
| WO | 2016/160602 A2 | 10/2016 |
| WO | 2016/201304 A1 | 12/2016 |
| WO | 2017/132202 A1 | 8/2017 |
| WO | 2018/005973 A1 | 1/2018 |
| WO | 2018/183169 A1 | 10/2018 |
| WO | 2020/205100 A1 | 10/2020 |

OTHER PUBLICATIONS

International Preliminary Report on Patentability Chapter 1 received for PCT Application Serial No. PCT/US20/19991 dated Sep. 30, 2021, 8 pages.
Konstantinidis et al., "Targeting IL-2 to the Endoplasmic Reticulum Confines Autocrine Growth Stimulation to NK-92 Cells", Experimental Hematology, 2005, vol. 33, No. 2, pp. 159-164 (Cited from Specification).
Brhuns et al., "Specificity and Affinity of Human Fcγ Receptors and their Polymorphic Variants for Human IgG Subclasses", Blood, 2009, vol. 113, No. 16, pp. 3716-3725 (Cited from Specification).
Kalaitsidou et al., "CAR T-Cell Therapy: Toxicity and the Relevance of Preclinical Models", Immunotherapy, 2015, vol. 7, No. 5, pp. 487-497 (Cited from Specification).
Niazi et al., "Activation of Human CD4+ T Cells by Targeting MHC Class II Epitopes to Endosomal Compartments Using Human CD1 Tail Sequences", Cancer Immunology Immunotherapy, 2012, vol. 122, pp. 522-531 (Cited from Specification).
Office Action received for Taiwanese Patent Application Serial No. 109106960 dated Mar. 22, 2021, 19 pages (Including English Translation).
Sadelain et al., "The basic principles of chimeric antigen receptor (CAR) design", Cancer Discovery, 2013, vol. 3, No. 4, 21 pages.
Lakna Panawala., "Difference Between NK Cells and NKT Cells", EPEDIAA, 2017, 6 pages.
International Search Report and Written Opinion received for PCT Application Serial No. PCT/US2020/019991 dated Jun. 30, 2020, 11 pages.
Kurys et al., 'The Long Signal Peptide Isoform and Its Alternative Processing Direct the Intracellular Trafficking of Interleukin-15', The Journal of Biological Chemistry, 2000, vol. 275, No. 39, pp. 30653-30659.
Fujii et al., "A potential therapy for chordoma via antibody-dependent cell-mediated cytotoxicity employing NK or high-affinity NK cells In combination with cetuximab", Journal of Neurosurgery, 2018, vol. 128, pp. 1419-1427.
Bergamaschi et al., "Secretion and Biological Activity of Short Signal Peptide IL-15 Is Chaperoned by IL-15 Receptor Alpha In Vivo",The Journal of Immunology, 2009, vol. 183, pp. 3064-3072.
Zhang et al., "Characterization of Interleukin-15 Gene-Modified Human Natural Killer Cells: Implications for Adoptive Cellular Immunotherapy", Haematologica, 2004, vol. 89, No. 3, pp. 338-347.
Sahm et al., "Expression of IL-15 in NK Cells Results in Rapid Enrichment and Selective Cytotoxicity of Gene-Modified Effectors That Carry a Tumor-Specific Antigen Receptor", Cancer Immunology Immunotherapy, 2012, vol. 61, pp. 1451-1461.

(Continued)

*Primary Examiner* — Scott Long
(74) *Attorney, Agent, or Firm* — Martin Fessenmaier; Umberg Zipser LLP

(57) ABSTRACT

Systems and methods are presented that provide for improved NK cell function. In preferred aspects, NK-92 cells express recombinant er/LSP-IL-15 to so render the NK-92 cells independent of exogenous cytokines and to provide extracellular immune stimulation.

20 Claims, 9 Drawing Sheets
Specification includes a Sequence Listing.

(56) References Cited

OTHER PUBLICATIONS

Office Action received for Taiwanese Patent Application Serial No. 109106960 dated Sep. 6, 2021, 4 pages (Including English Translation).

SEQUENCE LISTING

<160> NUMBER OF SEQ ID NOS: 7

<210> SEQ ID NO 1
<211> LENGTH: 635
<212> TYPE: DNA
<213> ORGANISM: Artificial Sequence
<220> FEATURE:
<223> OTHER INFORMATION: codon optimized IL-15

<400> SEQUENCE: 1

```
atgggatctg atctggggcc tcggtgcaca tgctttacat gtgtttagtc gaggttaaaa        60
aaacgtctag gccccccgaa ccacggggac gtggttttcc tttgaaaaac acgataaccg       120
```

```
ccaccatgcg catcagcaag ccccacctgc gcagcatcag catccagtgc tacctgtgcc      180
tgctgctgaa cagccacttc ctgaccgagg ccggcatcca cgtgttcatc ctgggctgct      240
tcagcgccgg cctgcccaag accgaggcca actgggtgaa cgtgatcagc gacctgaaga      300
agatcgagga cctgatccag agcatgcaca tcgacgccac cctgtacacc gagagcgacg      360 tgcacccag ctgcaaggtg accgccatga agtgcttcct gctggagctg caggtgatca      420
gcctggagag cggcgacgcc agcatccacg acaccgtgga gaacctgatc atcctggcca      480
acaacagcct gagcagcaac ggcaacgtga ccgagagcgg ctgcaaggag tgcgaggagc      540
tggaggagaa gaacatcaag gagttcctgc agagcttcgt gcacatcgtg cagatgttca      600
tcaacaccag cggctccgag aaggacgagc tgtaa                                 635
```

```
<210> SEQ ID NO 2
<211> LENGTH: 489
<212> TYPE: DNA
<213> ORGANISM: Artificial Sequence
<220> FEATURE:
<223> OTHER INFORMATION: long signal peptide variant (LSP-IL-15)

<400> SEQUENCE: 2
atgcgcatca gcaagcccca cctgcgcagc atcagcatcc agtgctacct gtgcctgctg       60
ctgaacagcc acttcctgac cgaggccggc atccacgtgt tcatcctggg ctgcttcagc      120
gccggcctgc ccaagaccga ggccaactgg gtgaacgtga tcagcgacct gaagaagatc      180
gaggacctga tccagagcat gcacatcgac gccaccctgt acaccgagag cgacgtgcac      240
cccagctgca aggtgaccgc catgaagtgc ttcctgctgg agctgcaggt gatcagcctg      300
gagagcggcg acgccagcat ccacgacacc gtggagaacc tgatcatcct ggccaacaac      360
agcctgagca gcaacggcaa cgtgaccgag agcggctgca aggagtgcga ggagctggag      420
gagaagaaca tcaaggagtt cctgcagagc ttcgtgcaca tcgtgcagat gttcatcaac      480
accagctaa                                                              489
```

```
<210> SEQ ID NO 3
<211> LENGTH: 162
<212> TYPE: PRT
<213> ORGANISM: Artificial Sequence
<220> FEATURE:
<223> OTHER INFORMATION: long signal peptide variant (LSP-IL-15) peptide
      seq

<400> SEQUENCE: 3

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
```

```
            115                 120                 125
Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser

<210> SEQ ID NO 4
<211> LENGTH: 510
<212> TYPE: DNA
<213> ORGANISM: Artificial Sequence
<220> FEATURE:
<223> OTHER INFORMATION: erIL-15 Long Signal Peptide nt seq

<400> SEQUENCE: 4
atgcgcatca gcaagcccca cctgcgcagc atcagcatcc agtgctacct gtgcctgctg      60
ctgaacagcc acttcctgac cgaggccggc atccacgtgt tcatcctggg ctgcttcagc     120
gccggcctgc ccaagaccga ggccaactgg gtgaacgtga tcagcgacct gaagaagatc     180
gaggacctga tccagagcat gcacatcgac gccaccctgt acaccgagag cgacgtgcac     240
cccagctgca aggtgaccgc catgaagtgc ttcctgctgg agctgcaggt gatcagcctg     300
gagagcggcg acgccagcat ccacgacacc gtggagaacc tgatcatcct ggccaacaac     360
agcctgagca gcaacggcaa cgtgaccgag agcggctgca aggagtgcga ggagctggag     420
gagaagaaca tcaaggagtt cctgcagagc ttcgtgcaca tcgtgcagat gttcatcaac     480
accagcggct ccgagaagga cgagctgtaa                                      510

<210> SEQ ID NO 5
<211> LENGTH: 169
<212> TYPE: PRT
<213> ORGANISM: Artificial Sequence
<220> FEATURE:
<223> OTHER INFORMATION: erIl-15 Long Signal Peptide peptide seq

<400> SEQUENCE: 5

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
                20                  25                  30

Val Phe Ile Leu Gly Cys Phe Ser Ala Gly Leu Pro Lys Thr Glu Ala
            35                  40                  45

Asn Trp Val Asn Val Ile Ser Asp Leu Lys Lys Ile Glu Asp Leu Ile
50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser Gly Ser Glu Lys Asp Glu Leu
```

```
<210> SEQ ID NO 6
<211> LENGTH: 408
<212> TYPE: DNA
<213> ORGANISM: Artificial Sequence
<220> FEATURE:
<223> OTHER INFORMATION: IL-15 Short Signal Peptide nt seq

<400> SEQUENCE: 6
atggtgctgg gcaccatcga cctgtgcagc tgcttcagcg ccggcctgcc caagaccgag      60
gccaactggg tgaacgtgat cagcgacctg aagaagatcg aggacctgat ccagagcatg     120
cacatcgacg ccaccctgta caccgagagc gacgtgcacc ccagctgcaa ggtgaccgcc     180
atgaagtgct tcctgctgga gctgcaggtg atcagcctgg agagcggcga cgccagcatc     240
cacgacaccg tggagaacct gatcatcctg gccaacaaca gcctgagcag caacggcaac     300
gtgaccgaga gcggctgcaa ggagtgcgag gagctggagg agaagaacat caaggagttc     360
ctgcagagct tcgtgcacat cgtgcagatg ttcatcaaca ccagctaa                  408

<210> SEQ ID NO 7
<211> LENGTH: 135
<212> TYPE: PRT
<213> ORGANISM: Artificial Sequence
<220> FEATURE:
<223> OTHER INFORMATION: IL-15 Peptide Seq

<400> SEQUENCE: 7

Met Val Leu Gly Thr Ile Asp Leu Cys Ser Cys Phe Ser Ala Gly Leu
1               5                   10                  15

Pro Lys Thr Glu Ala Asn Trp Val Asn Val Ile Ser Asp Leu Lys Lys
            20                  25                  30

Ile Glu Asp Leu Ile Gln Ser Met His Ile Asp Ala Thr Leu Tyr Thr
        35                  40                  45

Glu Ser Asp Val His Pro Ser Cys Lys Val Thr Ala Met Lys Cys Phe
    50                  55                  60

Leu Leu Glu Leu Gln Val Ile Ser Leu Glu Ser Gly Asp Ala Ser Ile
65                  70                  75                  80

His Asp Thr Val Glu Asn Leu Ile Ile Leu Ala Asn Asn Ser Leu Ser
                85                  90                  95

Ser Asn Gly Asn Val Thr Glu Ser Gly Cys Lys Glu Cys Glu Glu Leu
            100                 105                 110

Glu Glu Lys Asn Ile Lys Glu Phe Leu Gln Ser Phe Val His Ile Val
        115                 120                 125

Gln Met Phe Ile Asn Thr Ser
    130                 135
```

RECOMBINANT ERIL-15 NK CELLS

This application claims the benefit of priority to our U.S. provisional patent application with the Ser. No. 62/819,256, filed on Mar. 15, 2019, the contents of which are incorporated herein by reference in its entirety.

SEQUENCE LISTING

The content of the ASCII text file of the sequence listing named Sequence_listing_ST25, which is 8 kb in size was created on Feb. 19, 2020 and electronically submitted via EFS-Web along with the present application is incorporated by reference in its entirety.

FIELD OF THE INVENTION

The present disclosure relates to genetically modified immune cells expressing IL-15, especially as they relate to NK cells that express and intracellularly retain a modified IL-15 and that further express at least one of a high affinity variant of CD16 and a CAR (chimeric antigen receptor).

BACKGROUND OF THE INVENTION

The background description includes information that may be useful in understanding the present disclosure. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

NK-92 cells are desirable in various aspects of cell-based therapies as they lack apparent toxicity against allogeneic cells in a recipient and have a relatively broad spectrum of cytotoxic activity towards a wide range of tumor cells. Moreover, NK-92 cells can be cultivated in a relatively simple manner and as such present an attractive option for adoptive cancer immunotherapy. Unfortunately, proliferation and function of NK-92 cells are highly dependent on IL-2, which increases cost where NK-92 cells are needed at large scale. To circumvent problems associated with such cytokine requirements, NK-92 cells have been transformed to express and intracellularly retain IL-2 (see e.g., *Exp Hematol* 33:159-164). While such modified cells indeed became independent of exogenous cytokines, various disadvantages remained. Among other things, IL-2 released from such modified cells may increase IL-2 mediated effects in vivo where such cells are used in a mammal, which is particularly undesirable where IL-2 stimulates immune suppression in a tumor microenvironment (typically via growth and expansion of myeloid derived suppressor cells (MDSCs) and T-regulatory cells (Tregs)).

In another example, NK-92 cells were transfected to express IL-15 from a cDNA that was cloned into a pcDNA3 expression vector (see e.g., *Haematologica*, 2004; 89:338-347), and so transfected cells continuously produced high levels of IL-15 in the culture supernatant, which was thought to make the cells proliferate significantly more rapidly in response to stimulation with low doses of IL-2 or IL-15. Moreover, the cumulative number of cells in long-term culture was also significantly higher than with non-transfected cells. However, where such cells are used in vivo, the high levels of secreted IL-15 may become clinically problematic.

Similarly, NK-92 cells were transformed using a viral transfection system to express a recombinant native form of IL-15 (see e.g., *Cancer Immunol Immunother* (2012) 61:1451-1461). While such recombinant cells were able to grow in the absence of exogenous cytokines and expressed a recombinant CAR, transfection efficacy was relatively low, produced relatively low quantities of IL-15 intracellularly, and secreted low quantities of IL-15 into the culture medium. Moreover, cytotoxicity of the recombinant cells was reduced as compared to the parental NK-92 cell line. Notably, where the same IL-15 was expressed from a plasmid, so generated NK-92 cells were not fully independent from exogenous growth factors, thus limiting in vivo use of such recombinant cells.

Thus, even though various modified immune cells, and especially modified NK cells are known in the art, all or almost all of them suffer from various disadvantages. Consequently, there is a need to provide improved modified NK cells exhibit desirable growth characteristics while maintaining targeted cytotoxicity.

SUMMARY OF THE INVENTION

Various recombinant cells, compositions, and methods are disclosed herein where an NK cell is genetically modified to express intracellularly and secrete or present IL-15 or a variant thereof to so render the modified NK cell independent from exogenous cytokines, and to allow for stimulation/activation of other immune competent cells that are in proximity to the modified NK cell.

In one aspect of the inventive subject matter, the inventors contemplate a genetically modified NK cell and methods of making such cell wherein the genetically modified NK cell comprises a recombinant nucleic acid that includes a first segment encoding erLSP-IL-15. Most typically, the NK cell is an NK-92 cell, and the recombinant nucleic acid is a DNA (e.g., linearized plasmid). Preferably, but not necessarily, the IL-15 portion in the erLSP-IL-15 comprises a codon-optimized human IL-15 sequence In further embodiments, the recombinant nucleic acid further comprises a second segment encoding CD16 or a high affinity CD16, and/or may further comprise a third segment encoding a chimeric antigen receptor, and/or may further comprise a fourth segment encoding a protein that interferes with checkpoint inhibition, that provides immune stimulation, a protein that binds/inhibits a cytokine involved with immune suppression, and/or a IL-15 receptor alpha chain. It is also contemplated that the recombinant nucleic acid comprises a promotor having a sufficient strength to drive expression of the erLSP-IL-15 in an amount sufficient to (a) render the modified NK cell independent from exogenous cytokines, and to (b) allow for stimulation/activation of other immune competent cells that are in proximity to the modified NK cell. Optionally, the modified NK cell may comprise an antibody that is coupled to the cell via CD16.

In a further aspect of the inventive subject matter, the inventors also contemplate pharmaceutical composition that comprises a pharmaceutically acceptable carrier in combination with a genetically modified NK cell as described herein. Most typically, such compositions will be formulated for transfusion to a patient and may include at least $1\times10^9$ cells per dosage unit.

Therefore, the inventors also contemplate the use of a genetically modified NK cell as described herein in the treatment of cancer. While such use may be a transfusion of the cells as a stabd-alone treatment, other contemplated uses will also comprise administration of a drug that breaks into the TME, administration of a drug that reduces immune suppression, administration of a drug that stimulated an immune competent cell, administration of a cancer vaccine composition, and/or administration of a drug that helps maintain an immune response and promotes memory cell development.

Various objects, features, aspects, and advantages will become more apparent from the following detailed description of preferred embodiments, along with the accompanying drawing in which like numerals represent like components.

DETAILED DESCRIPTION

Figure 1:
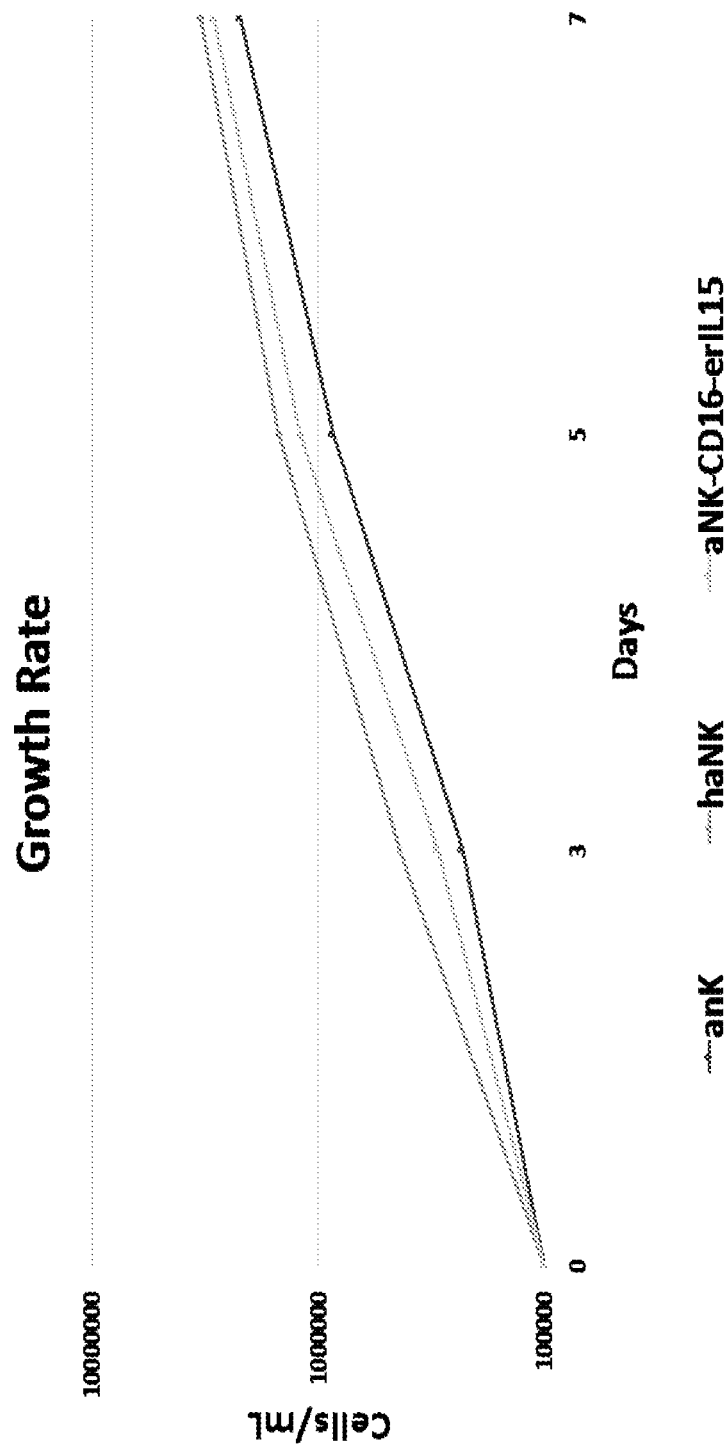
FIG. 1 depicts an exemplary graph illustrating growth rates of various NK cells as indicated.

The inventors have now discovered that modified NK cells can be generated that produce quantities of recombinant IL-15 sufficient to provide IL-2/IL-15 independent growth and stimulation while maintaining cytotoxicity and functional expression of recombinant CD16 and/or CAR. Moreover, in at least some embodiments, contemplated modified NK cells will not only produce sufficient intracellular IL-15 (and especially erLSP-IL-15) to allow for growth and expansion in the absence of cytokines, but also allow for secretion of IL-15 in an amount that assists in immune stimulation (or reversion of immune suppression) in the tumor microenvironment (TME) when such cells are present in the TME. Thus, NK cells according to the inventive subject matter will advantageously allow for simplified culture and expansion while providing an avenue for recombinant targeted cytotoxicity via CD 16 and/or CAR.

Previously prepared NK-92 derivatives that expressed IL-2 with an endoplasmatic retention sequence were suspected to support the growth and expansion of immune suppressor cells such as myeloid derived suppressor cells (MDSC) and T-regulatory cells (T-regs). These negative regulators can mitigate any antitumor effect of the immune cells and in particular aNK, haNK and t-haNK as well as donor NK-cells. Recombinant IL-15 on the other hand only supports the function of immune active cells without the negative effects of erIL-2.

However, it should be appreciated that expression of IL-15 and variants thereof may adversely affect growth and/or function of NK cells, and especially NK-92 cells. Nor can expression of a biologically active form of IL-15 and variants thereof be expected, especially in quantities that support cell expansion and activity without adverse interference with recombinant proteins also desired for targeted NK cells such as CD16 and/or CAR. Still further, overexpression and secretion of IL-15 and variants thereof beyond immune stimulatory levels may result in systemic side effects in the recipient of such cells. Viewed from a different perspective, preferred modified NK cells will produce and secret IL-15 that is sufficiently low to avoid systemic side effects but to maintain the desired beneficial effects growth and stimulatory properties for the modified cells and immune cells within the TME. Notably, the inventors now discovered that NK cells can be prepared that have a desirable balance between intracellularly formed and retained IL-15 to stimulate growth and expansion in an autocrine manner (i.e., without the need of exogenous cytokines) and secreted IL-15 that provides immune stimulatory effect on other immune competent cells within a TME.

With respect to suitable NK cells it is generally contemplated that the NK cells may be autologous NK cells from a subject that will receive the genetically modified NK cells. Such autologous NK cells may be isolated from whole blood, or cultivated from precursor or stem cells using methods well known in the art. However, it should also be appreciated that the NK cells need not be autologous, but may be allogenic or heterologous NK cells. In particularly preferred aspects of the inventive subject matter, the NK cells that are genetically engineered are NK-92 cells or derivatives thereof. For example, in one particularly preferred aspect of the inventive subject matter, the genetically engineered NK cell is an NK-92 derivative that is modified to have reduced or abolished expression of at least one killer cell immunoglobulin-like receptor (KIR), which will typically render such cells constitutively activated (via lack of or reduced inhibition).

NK-92 cells exhibit an unusual receptor expression profile, expressing a relatively large number of activating (e.g., NKp30, NKp46, 2B4, NKGD, E, CD28) receptors. Conversely, NK-92 cells also expresses few inhibitory receptors (e.g., NKGA/B, low levels of KIR2DL4, ILT-2), and lack most of the killer inhibitory receptors (KIRs) clonally expressed on normal NK cells. In addition, NK-92 expresses relatively high levels of molecules involved in the perforin-granzyme cytolytic pathway as well as additional cytotoxic effector molecules including tumor necrosis factor (TNF)-superfamily members FasL, TRAIL, TWEAK, TNF-alpha, indicating the ability to kill via alternative mechanisms. Moreover, NK-92 cells also express other molecules implicated immune effector cell regulation (CD80, CD86, CD40L, TRANCE) whose relevance in NK killing is unclear. Notably, however, these particularly desirable traits will not be adversely affected by the modifications described herein. Indeed, in at least some embodiments, one or more of the above activator and/or effector proteins may be over-expressed in response to intracellular expression of IL-15 as noted in more detail below.

Moreover, suitable NK cells may have one or more modified KIR that are mutated such as to reduce or abolish interaction with MEW class I molecules. Of course, it should be noted that one or more KIRs may also be deleted or expression may be suppressed (e.g., via miRNA, siRNA, etc.). Most typically, more than one KIR will be mutated, deleted, or silenced, and especially contemplated KIR include those with two or three domains, with short or long cytoplasmic tail. Viewed from a different perspective, modified, silenced, or deleted KIRs will include KIR2DL1, KIR2DL2, KIR2DL3, KIR2DL4, KIR2DL5A, KIR2DL5B, KIR2DS1, KIR2DS2, KIR2DS3, KIR2DS4, KIR2DS5, KIR3DL1, KIR3DL2, KIR3DL3, and KIR3DS1. Such modified cells may be prepared using protocols well known in the art. Alternatively, such cells may also be commercially obtained from NantKwest (see URL www.nantkwest.com) as aNK cells (activated natural killer cells). Such cells may then be additionally genetically modified to express IL-15 or a variant thereof as further discussed below.

In another preferred aspect of the inventive subject matter, the genetically engineered NK cell may also be an NK-92 derivative that is modified to express the high-affinity Fcγ receptor (CD16). Sequences for high-affinity variants of the Fcγ receptor are well known in the art (see e.g., *Blood* 2009 113:3716-3725), and all manners of generating and expression are deemed suitable for use herein. Expression of such receptor is believed to allow specific targeting of tumor cells using antibodies that are specific to a patient's tumor cells (e.g., neoepitopes), a particular tumor type (e.g., her2neu, PSA, PSMA, etc.), or that are associated with cancer (e.g., CEA-CAM). Advantageously, such antibodies are commercially available and can be used in conjunction with the cells (e.g., bound to the Fcγ receptor). Alternatively, such cells may also be commercially obtained from NantKwest as haNK cells ('high-affinity natural killer cells). Such cells may then be further genetically modified to express IL-15 or a variant thereof as further discussed below.

Alternatively, or additionally, the genetically engineered NK cell may also be genetically engineered to express a chimeric antigen receptor (CAR). In especially preferred aspects, the CAR will have a scFv portion or other ectodomain with binding specificity against a tumor associated antigen, a tumor specific antigen, and a cancer neoepitope. Thus, as will be readily appreciated, suitable CARs will include first, second, and third generation CARs (see e.g., *Immunotherapy* (2015) 7(5):487-497). As noted before, there are numerous manners of genetically engineering an NK cell to express such chimeric T-cell receptor, and all manners are deemed suitable for use herein. Alternatively, such cells may also be commercially obtained from NantKwest as taNK cells ('target-activated natural killer cells'). Such cells may then be further genetically modified to express IL-15 or a variant thereof as further discussed below.

Where the cells are engineered to have affinity towards a cancer associated antigen or antibody with specificity towards a cancer associated antigen, it is contemplated that all known cancer associated antigens are considered appropriate for use. For example, cancer associated antigens include CEA, MUC-1, CYPB1, etc. Likewise, where the cells are engineered to have affinity towards a cancer specific antigen or antibody with specificity towards a cancer specific antigen, it is contemplated that all known cancer specific antigens are considered appropriate for use. For example, cancer specific antigens include PSA, Her-2, PSA, brachyury, etc. Where the cells are engineered to have affinity towards a cancer neoepitope or antibody with specificity towards a cancer neoepitope, it is contemplated that all known manners of identifying neoepitopes will lead to suitable targets. For example, neoepitopes may be identified from a patient tumor in a first step by whole genome analysis of a tumor biopsy (or lymph biopsy or biopsy of a metastatic site) and matched normal tissue (i.e., non-diseased tissue from the same patient) via synchronous comparison of the so obtained omics information. So identified neoepitopes can then be further filtered for a match to the patient's HLA type to increase likelihood of antigen presentation of the neoepitope. Most preferably, such matching can be done in silico.

With respect to suitable IL-15 sequences for expression it is generally preferred that the IL-15 is a mammalian IL-15 sequence, and most preferably a human IL-15 sequence (see e.g., UniProt identifier P40933). Moreover, it is noted that suitable IL-15 sequences include various variants, and especially contemplated variants include those with a long signal peptide (LSP) and short signal peptide (SSP). The LSP variant has typically a signal peptide of 48 amino acids and the transcript typically includes a 316 bases 5'-untranslated region (UTR), a 486 bases coding sequence, and a C-terminal 3'-UTR region that is about 400 bases in length. The SSP variant has typically a short signal peptide of 21 amino acids which is based on alternative splicing (encoded by exons 4A and 5). Notably, both isoforms produce the same mature protein, however cellular trafficking is distinct. More specifically, the IL-15 LSP isoform was detected in the Golgi apparatus, early endosomes, and endoplasmic reticulum, and can occur in secreted and membrane-bound form. On the other hand, the IL-15 SSP isoform is not secreted and it seems to be restricted to the cytoplasm and nucleus where that isoform appears to be involved in the regulation of the cell cycle. Still further contemplated IL-15 variants include superagonist variants, and especially IL-15 N72D mutants, which may or may not include additional signal peptides and/or trafficking signals as discussed below.

Based on the apparent differential signaling, the inventors contemplate therefore use of various modifications to the recombinant IL-15 to so effect proper expression levels and distribution within the cell and amount secreted. To that end, the inventors contemplate use of various signaling moieties that can be fused to the recombinant IL-15. For example, where the IL-15 or IL-15 variant is to be exported to the endosomal and lysosomal compartment, a leader peptide such as the CD1b leader peptide may be employed to sequester the (nascent) protein from the cytoplasm. Additionally, or alternatively, targeting presequences and/or targeting peptides can be employed. The presequences of the targeting peptide may be added to the N-terminus and/or C-terminus and typically comprise between 6-136 basic and hydrophobic amino acids. In case of peroxisomal targeting, the targeting sequence may be at the C-terminus. Other signals (e.g., signal patches) may be used and include sequence elements that are separate in the peptide sequence and become functional upon proper peptide folding. In addition, protein modifications like glycosylations can induce targeting. Among other suitable targeting signals, the inventors contemplate peroxisome targeting signal 1 (PTS1), a C-terminal tripeptide, and peroxisome targeting signal 2 (PTS2), which is a nonapeptide located near the N-terminus.

In addition, sorting of proteins to endosomes and lysosomes may also be mediated by signals within the cytosolic domains of the proteins, typically comprising short, linear sequences. Some signals are referred to as tyrosine-based sorting signals and conform to the NPXY or YXXØ consensus motifs. Other signals known as dileucine-based signals fit [DE]XXXL[LI] or DXXLL consensus motifs. All of these signals are recognized by components of protein coats peripherally associated with the cytosolic face of membranes. YXXØ and [DE]XXXL[LI] signals are recognized with characteristic fine specificity by the adaptor protein (AP) complexes AP-1, AP-2, AP-3, and AP-4, whereas DXXLL signals are recognized by another family of adaptors known as GGAs. Also FYVE domain can be added, which has been associated with vacuolar protein sorting and endosome function. In still further aspects, endosomal compartments can also be targeted using human CD1 tail sequences (see e.g., *Immunology*, 122, 522-531). For example, lysosomal targeting can be achieved using a LAMP1-TM (transmembrane) sequence, while recycling endosomes can be targeted via the CD1a tail targeting sequence, and sorting endosomes can be targeted via the CD1c tail targeting sequence.

Trafficking to or retention in the cytosolic compartment may not necessarily require one or more specific sequence elements. However, in at least some aspects, N- or C-terminal cytoplasmic retention signals may be added, including a membrane-anchored protein or a membrane anchor domain of a membrane-anchored protein such that the protein is retained in the cell facing the cytosol. For example, membrane-anchored proteins include SNAP-25, syntaxin, synaptoprevin, synaptotagmin, vesicle associated membrane proteins (VAMPs), synaptic vesicle glycoproteins (SV2), high affinity choline transporters, neurexins, voltage-gated calcium channels, acetylcholinesterase, and NOTCH.

In still further contemplated aspects of the inventive subject matter, the IL-15 or IL-15 variant may also comprise one or more transmembrane segments that will direct the neoepitope after processing to the outside of the cell membrane to so be visible to immune competent cells. There are numerous transmembrane domains known in the art, and all of those are deemed suitable for use herein, including those having a single alpha helix, multiple alpha helices, alpha/beta barrels, etc. For example, contemplated transmembrane domains can comprise comprises the transmembrane region (s) of the alpha, beta, or zeta chain of the T-cell receptor, CD28, CD3 epsilon, CD45, CD4, CD5, CD8 (e.g., CD8 alpha, CD8 beta), CD9, CD16, CD22, CD33, CD37, CD64, CD80, CD86, CD134, CD137, CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R a, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, or PAG/Cbp.

In addition, it is also contemplated that the IL-15 or IL-15 variant may also be co-expressed with an IL-15 receptor alpha subunit. Such co-expression is deemed to allow binding or other association of the IL-15 or IL-15 variant with the receptor alpha chain to stabilize the IL-15 or IL-15 variant and/or assist in secretion or trafficking/presentation of the IL-15 or IL-15 variant on the surface of the modified NK cell. Similarly, various other proteins (besides a CD16 and/or CAR may be co-expressed with the IL-15 or IL-15 variant, and suitable co-expressed proteins include various immune modulatory compounds, and especially compounds that interfere with checkpoint inhibition (e.g., scFv against PD1, PD-L1, CTLA4, etc.), immune stimulation (e.g., IFN-γ, IL-12, IL-21, etc.) and/or compounds that bind/inhibit cytokines involved with immune suppression (e.g. TGF-β, IL-8, etc.).

As will be readily appreciated, the IL-15 or IL-15 variant and other co-expressed proteins will be encoded on a recombinant nucleic acid, which may be one or more recombinant RNA or DNA molecules. Most typically, however, the recombinant nucleic acid will be a polycistronic DNA construct, and preferably a plasmid. However, various other constructs are also deemed suitable for use herein and include viral vectors (which may be transfected as a virus or via other methods), linearized DNA, DNA bound to a carrier (e.g., for ballistic transfection), etc.

Regardless of the particular configuration and type of nucleic acid, it is generally preferred that the modified NK-92 cells will express the IL-15 or IL-15 variant in an amount sufficient to (a) render the so transfected cells independent from exogenous cytokines, and (b) allow for stimulation/activation of other immune competent cells that are in proximity to the transfected cells (typically within the TME). For example, it is contemplated that secreted or otherwise extracellular (or extracellularly presented) recombinant IL-15 or IL-15 variant will account for between 5-10%, or between 10-20%, or between 20-30%, or between 30-50% of total IL-15 or IL-15 variant produced in the cell. Thus, and viewed from a different perspective, secreted or otherwise extracellular (or extracellularly presented) recombinant IL-15 or IL-15 variant may be present in an amount of between about 20-60 pg/ml, or between about 60-80 pg/ml, or between about 80-100 pg/ml, or between about 100-150 pg/ml, or between about 150-200 pg/ml, or even higher. On the other hand, it is contemplated that the intracellularly retained IL-15 or IL-15 variant will be present an amount of between about 100-150 pg/ml, or between about 150-250 pg/ml, or between about 250-500 pg/ml, or between about 500-750 pg/ml, or even higher. Thus, it should be noted that particularly preferred modified NK-92 cells will produce recombinant IL-15 or IL-15 variant in sufficient quantities to support autonomous growth and stimulate immune competent cells in the TME as well as to stimulate establishment and maintenance of CD8+ T cell memory, but that such quantities are insufficient to trigger a systemic adverse event in a patient receiving such cells.

Therefore, from a functional perspective, the recombinant IL-15 or IL-15 variant will be present to stimulate or enhance effector functions and/or proliferation of other NK-cells (e.g., autologous NK cells in a TME), various T cells, etc., as well as enhance or trigger Jak/STAT signaling in cells in the TME. Moreover, due to the fraction of intracellularly retained IL-15 or IL-15 variant, such cells will also be able to proliferate in the complete absence of exogenous IL-2 and/or IL-15 as is described in more detail below. In yet further contemplated aspects, such modified NK-92 cells will also have an increased sensitivity to IL-12 signaling as compared to unmodified NK-92 cells, which may reduce IL-4 mediated suppression of IFN-γ, which in turn may reduce suppression of Th1 T cells in the TME.

Use of contemplated modified NK cells is preferably in the treatment of diseases responsive to administration of NK cells, and especially in the treatment of various cancers. As will be readily appreciated, the modified NK cells may be administered as a sole treatment agent, or as an agent in a more complex regimen. For example, the modified NK cells may be part of an immune therapy strategy in which a tumor may first be treated with drugs that break into the TME (e.g., abraxane), with drugs that reduce immune suppression (e.g., cytoxan), with drugs that stimulate various immune competent cells (e.g., ALT-803), with cancer vaccine compositions (e.g., recombinant AdV encoding tumor neoantigens), and/or with drugs that help maintain an immune response and promote memory cell development (e.g., tumor targeted IL-12). Exemplary suitable treatment regimens are discussed in WO 2018/005973, incorporated by reference herein.

With respect to suitable dosages and modes of administration, it is generally preferred that the quantity of cells and schedule of transfusion will typically follow established protocols known for NK cell transfusion. Therefore, typical quantities of modified NK-92 cells will be between $5 \times 10^7$ cells/dose IV and $5 \times 10^8$ cells/dose IV, or between $5 \times 10^8$ cells/dose IV and $5 \times 10^9$ cells/dose IV, or between $5 \times 10^9$ cells/dose IV and $5 \times 10^{10}$ cells/dose IV, and most typically between $7 \times 10^8$ cells/dose IV and $7 \times 10^9$ cells/dose IV (e.g., $2 \times 10^9$ cells/dose IV). Of course, it should be appreciated that where the modified NK cells express CD16 or a high-affinity variant of CD16 (e.g., 158V), the cells may be co-administered with one or more antibodies that will advantageously be bound to the modified NK cells (either in vitro prior to transfusion or sequentially, e.g., with antibody administered prior to cell transfusion).

EXAMPLES

The following examples are provided for representative guidance only and should not be understood to be limiting the inventive subject matter. Unless otherwise noted, all recombinant expression constructs used a codon-optimized version of IL-15 as shown as SEQ ID NO:1, which in at least some embodiments provided a higher yield of recombinant protein (data not shown).

In a first set of experiments, three variants of IL-15 were created using SEQ ID NO:1: a long signal peptide variant (LSP-IL-15), which corresponds to wild-type IL-15, a long signal peptide with ER-retention signal variant (erLSP-IL15), and a short signal peptide variant (SSP-IL-15), which is an alternate splice variant. More particularly, in one embodiment, IL-15 LSP had the nucleotide sequence as illustrated in SEQ ID NO:2; IL-15 LSP had the peptide sequence of SEQ ID NO:3; erIL-15 LSP had the nucleotide sequence of SEQ ID NO:4; erIL-15 LSP had the peptide sequence of SEQ ID NO:5; IL-15 SSP had the nucleotide sequence of SEQ ID NO:6; IL-15 had the peptide sequence of SEQ ID NO:7.

Plasmid Design and Transfection:

Three gBlocks flanked by KpnI/NotI restriction enzymes sites were synthesized by Integrated DNA Technologies and used to sub-clone each sequence into a similarly digested pNEUkv1-CD16-erIL2 plasmid backbone to create the following plasmids.

pNEUkv1-CD16 (158V)-IRES-(KpnI)-[IL-15 LSP]-(NotI)

pNEUkv1-CD16 (158V)-IRES--(KpnI)-[erIL-15 LSP]-(NotI)

pNEUkv1-CD16 (158V)-IRES--(KpnI)-[IL-15 SSP]-(NotI)

All plasmids were confirmed by Sanger sequencing, linearized by a SalI restriction enzyme digest and isolated by column-purification. Cell lines were created by electroporating 1 μg linearized DNA/$10^6$ cells using the MaxCyte GT electroporator (program NK-92-2-OC). pNEUkv1-CD16-IRES-[erIL-2] was similarly prepared and electroporated as a positive control. This experiment was repeated twice to confirm results. NK-92 cell lines co-expressing CD16 and erIL-15 were created by electroporation of the following linearized plasmids aNK (NK-92 "wildtype"): pNEUkv1-CD16 (158V)-IRES-[LSP IL-15]; pNEUkv1-CD16 (158V)-IRES-[erIL-15]; and pNEUkv1-CD16 (158V)-IRES-[SSP IL-15]. Positive control was transfected with pNeukv1-CD16-IRES-[erIL-2]. All samples were incubated in X-vivo-10/5% HS for 2 weeks in the absence of any cytokine.

To determine successful transfection of the plasmid, the electroporated cells were grown in X-vivo-10 with 5% HS for 2 weeks in the absence of any cytokine. Notably, only one of the three tested IL-15 clones grew back successfully: Long signal peptide with ER-retention signal (erIL-15). Moreover, as is shown in more detail below, NK-92 cells expressing erIL-15 (erLSP-IL15) maintained all relevant NK surface markers and cytotoxicity. Moreover, these cells also provided for desirable quantities of extracellular erLSP-IL15, which retained its biological function of immune stimulation, most likely after removal of the er/LSP segment from the mature IL-15.

Figure 2:
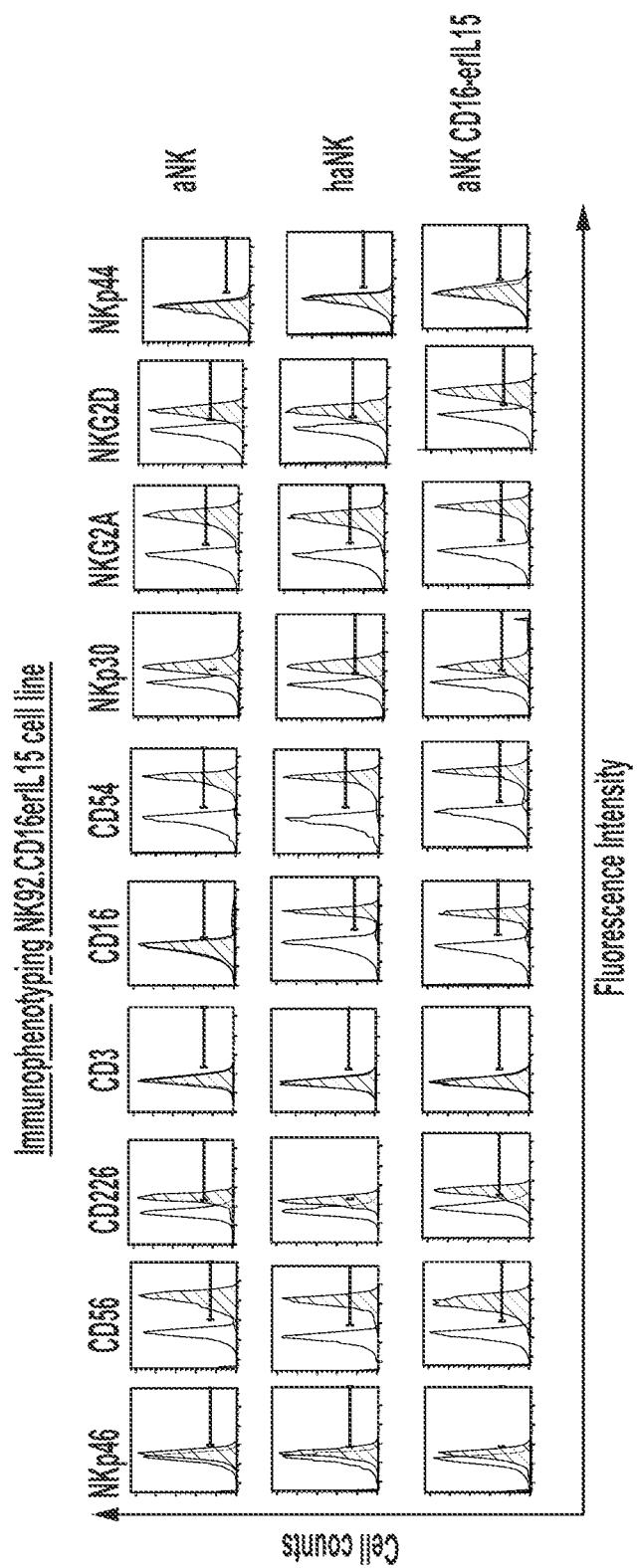
FIG. 2 depicts exemplary results from immunophenotyping of NK cells as indicated.

As can be seen from FIG. 1, Expression of erIL-15 did not change the growth rate of the erLSP-IL-15 expressing cells in the absence of exogenous cytokines compared to aNK or haNK (CD16+, erIL-2) cells. Thus, recombinant expression of erLSP-IL-15 advantageously provides sufficient autocrine signaling to support cell expansion. Such result is unexpected as the ER retention sequence is likely not removed within the cell, but still maintained proper function. Moreover, recombinant expression of erLSP-IL-15 did also not adversely affect numerous phenotypical markers of the modified N-92 cells. Exemplary results from immunophenotyping of the newly generated cell line is shown in FIG. 2. Here, the tested flow-cytometric surface receptor profiles were identical to haNK cells, a CD16-expressing NK-92 cell line that co-expresses erIL2.

Figure 3:
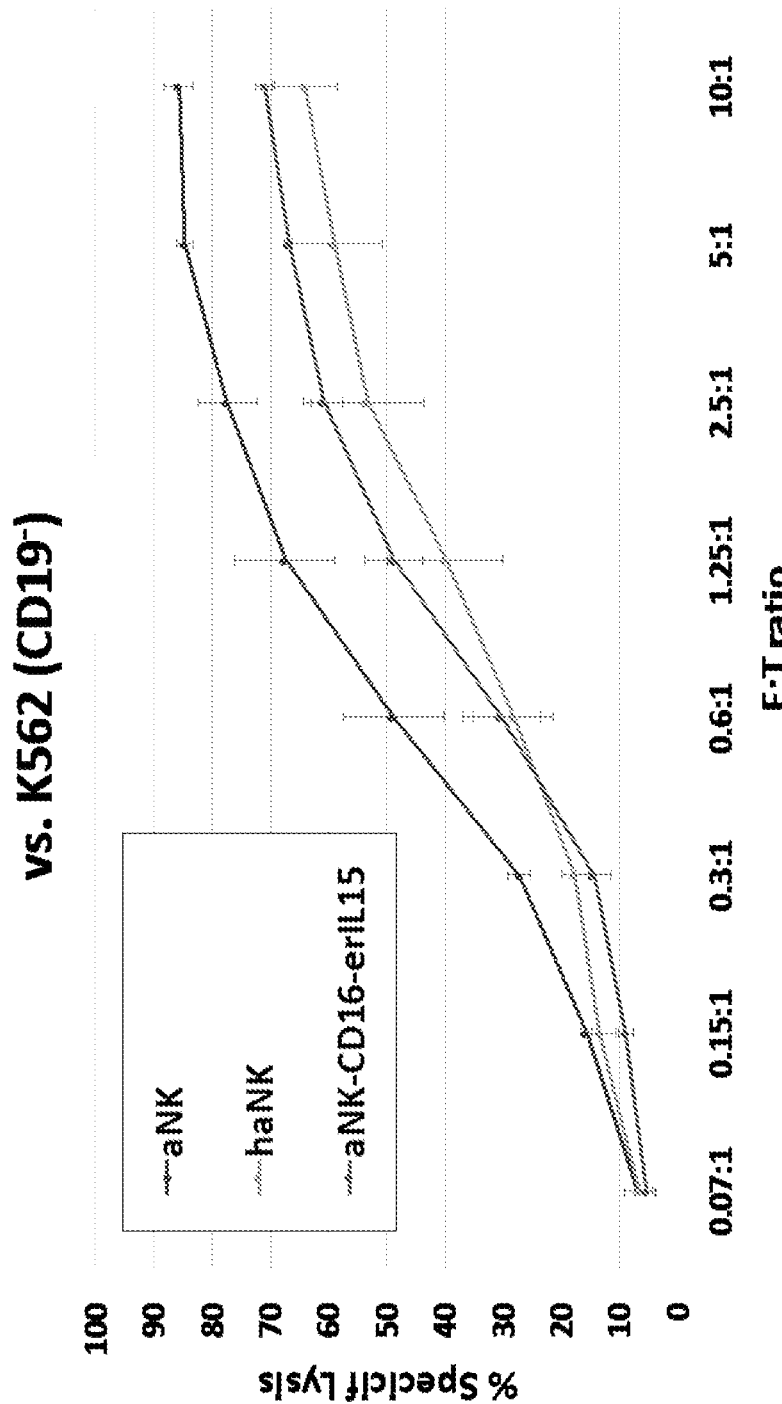
FIGS. 3-5 depict exemplary results for cytotoxicity of various NK cells as indicated.
Figure 4:
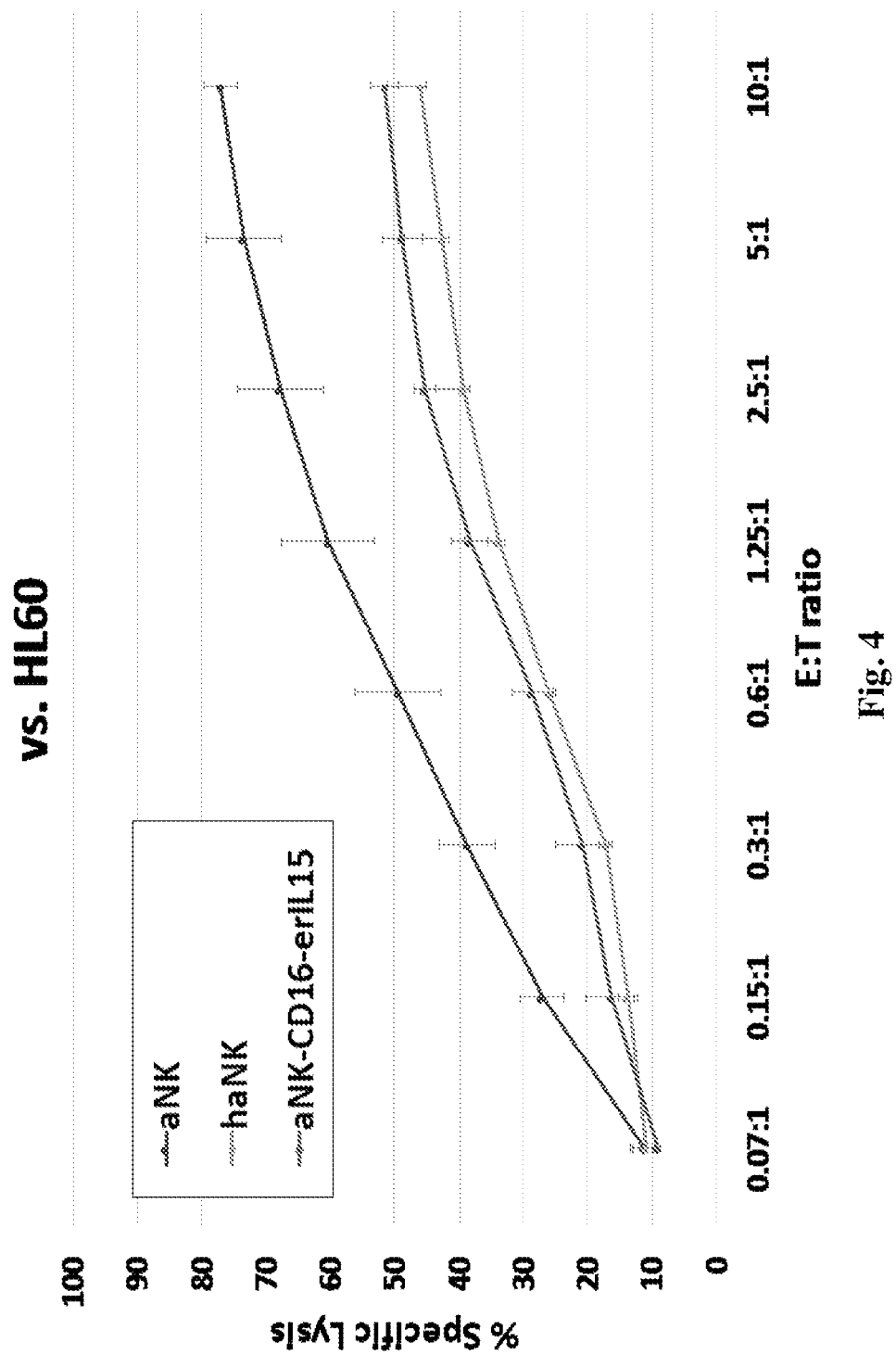
Figure 5:
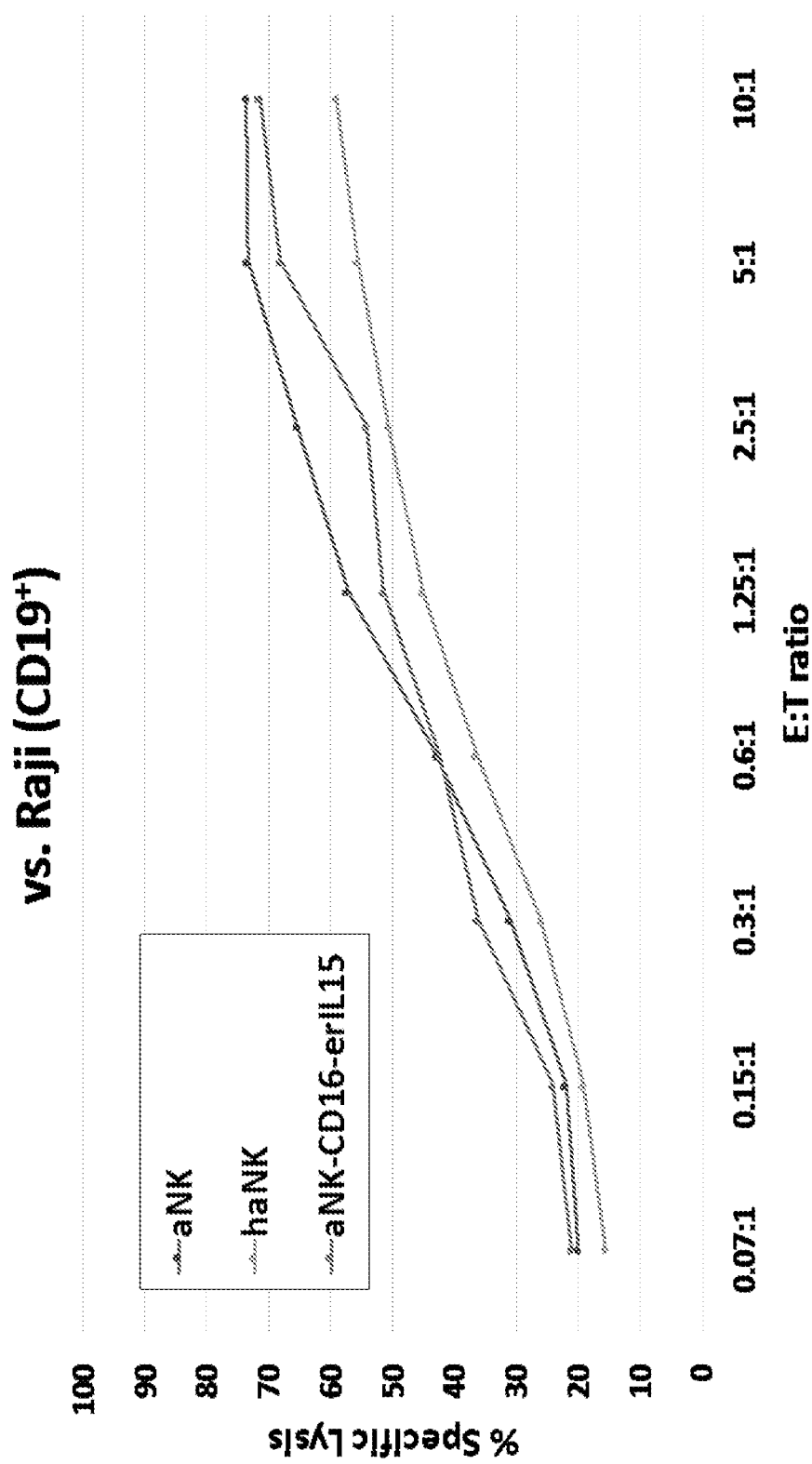

In this context, it should be appreciated that the newly created cell line maintained full expression of functionally critical surface proteins: CD16 (Fc receptor) and the activating receptor NKG2D. To test the functionality of the erIL-15 expressing cell line, and for comparison with an erIL-2 expressing cell line (haNK), cytotoxicity assays were performed using different target cell lines: K562, Raji and HL-60. The results shown in FIGS. 3-5 clearly establish that the introduction of the erIL-15 did not change the spontaneous cytotoxic properties in comparison to haNK cells. This is an unexpected finding as the integration of a novel/different gene could affect the cytotoxic function of the NK-92 cells. Notably, as can also be seen from FIGS. 3-5, erIL-15 expressing cells outperformed erIL-2 expressing cells at the same effector to target cell ratios.

Figure 6:
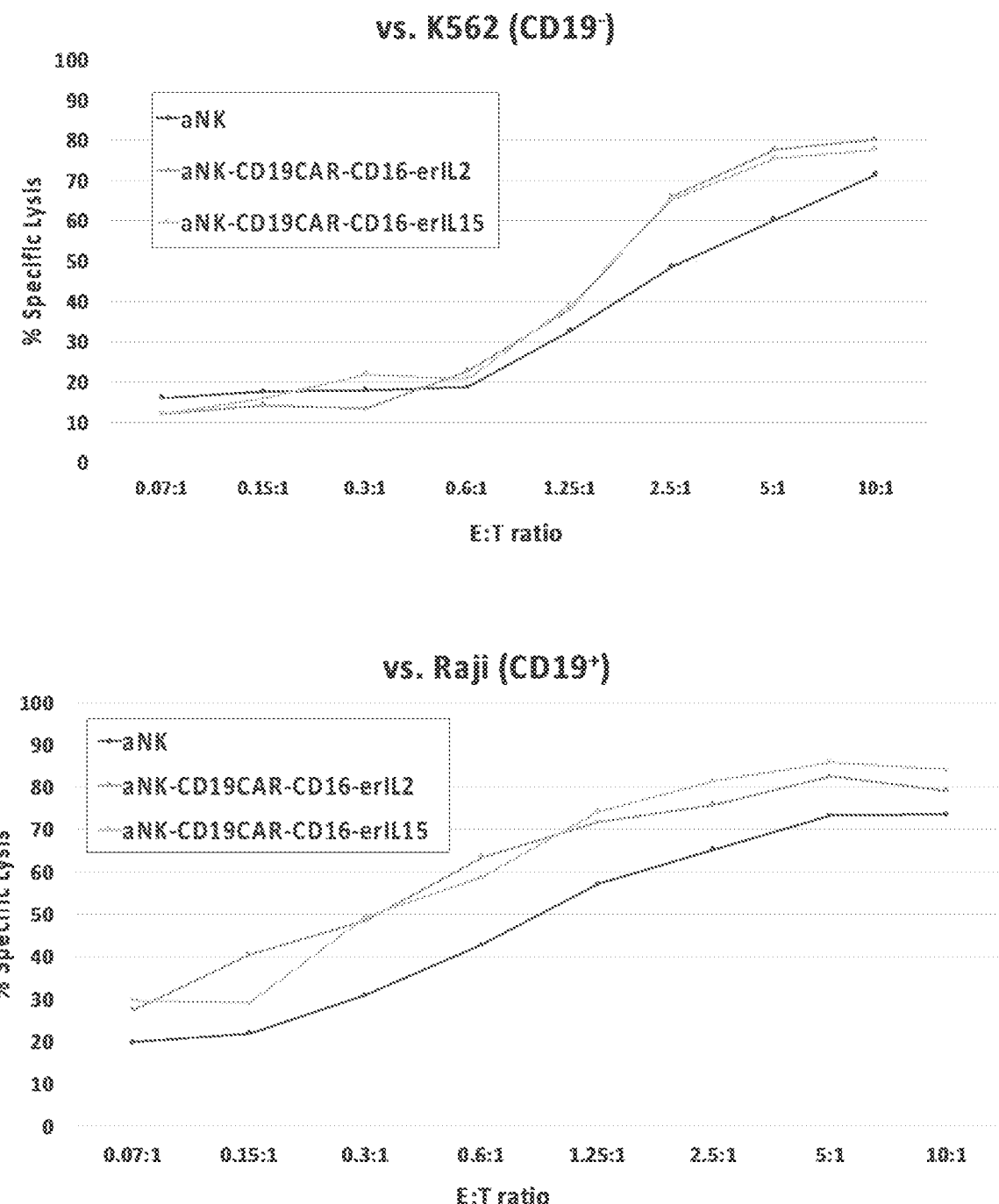
FIGS. 6-8 depict further exemplary results for cytotoxicity of various NK cells as indicated.
Figure 7:
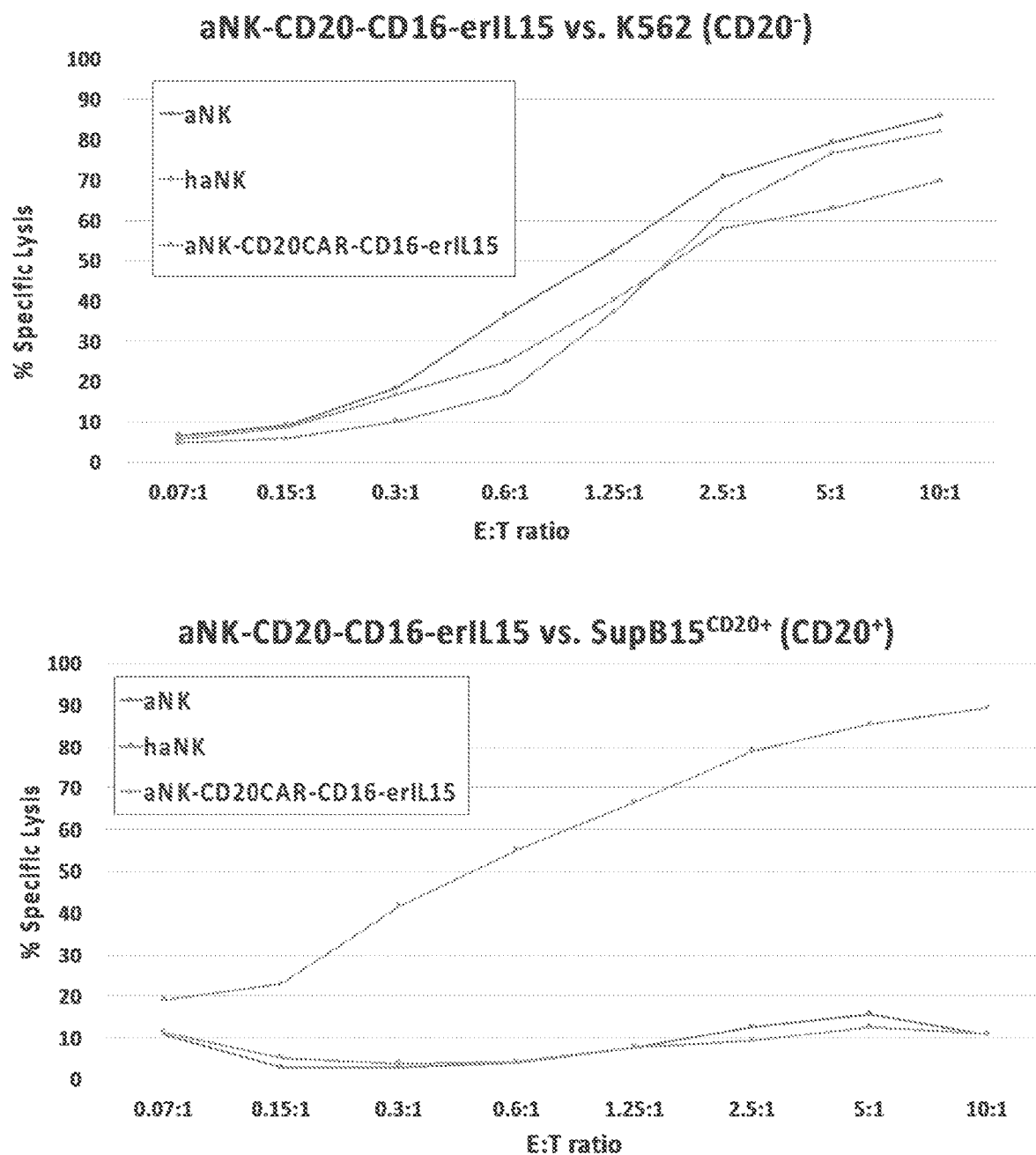
Figure 8:
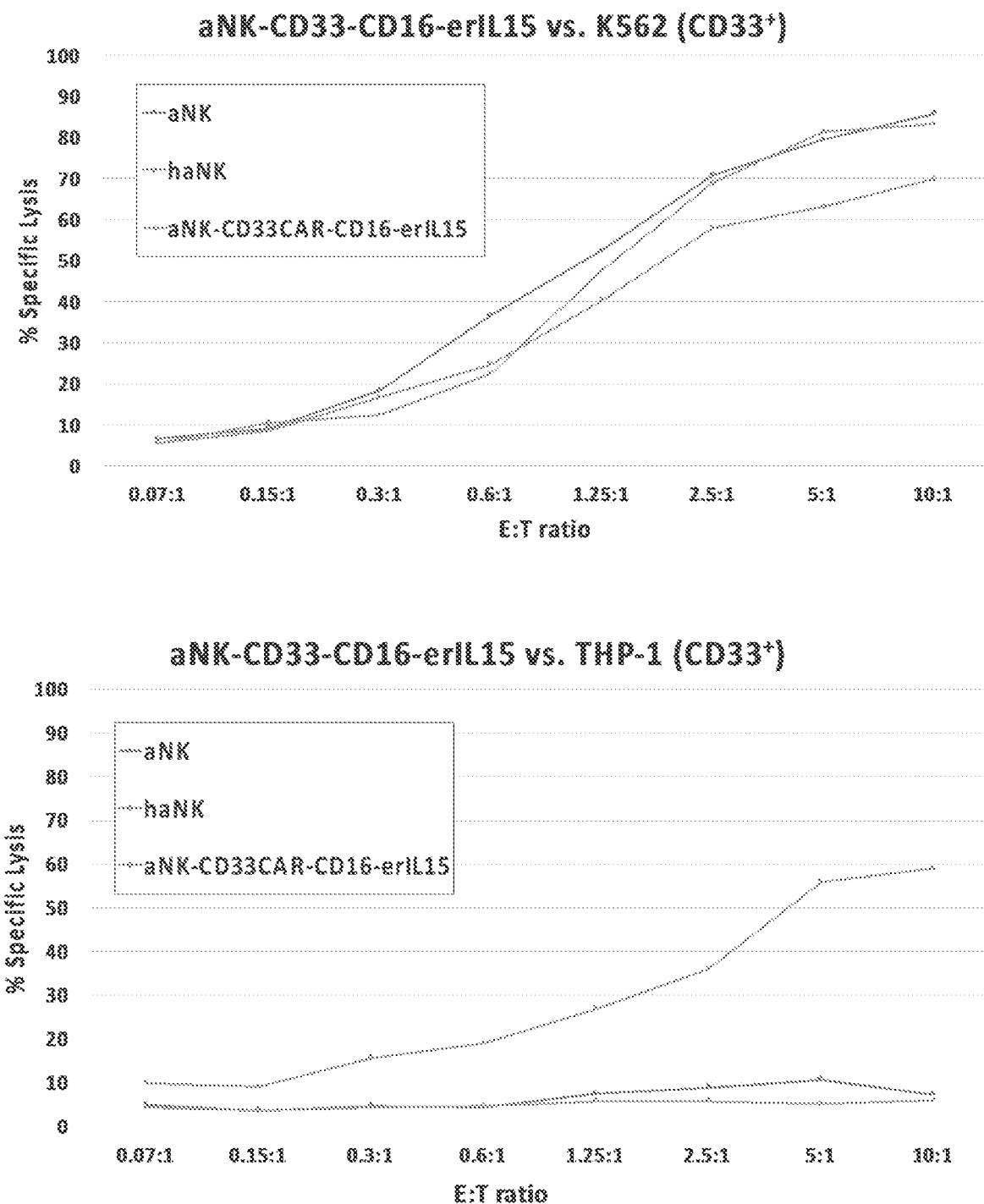
Figure 9:
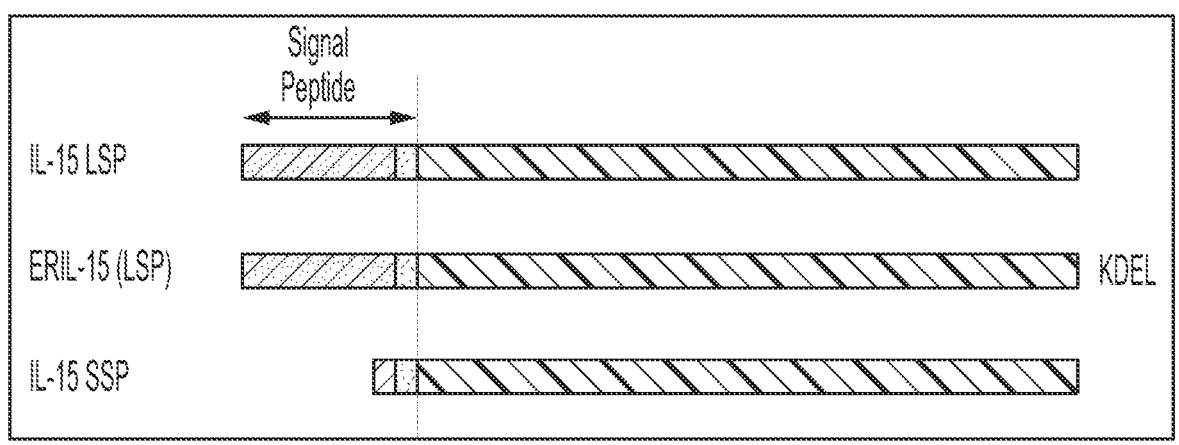
FIG. 9 depicts a schematic arrangement of exemplary recombinant nucleic acids used herein.

To further test whether the new erIL-15 based plasmid could be incorporated into a tricistonic CAR expressing plasmid without affecting the activity of the CAR, NK-92 cell lines were generated by electroporation with tricistronic CAR_CD16_erIL-15 plasmids coding for CD19CAR, CD20CAR, or CD33CAR. The cytotoxic function of erIL-15 expressing lines was tested and compared with that of the corresponding t-haNK cells (erIL-2) against several target cell lines: K562 (CD19neg, CD20neg, CD33+), SUPB15$^{CD20}$ (CD20+), and THP-1 (CD33+). FIGS. 6-8 illustrate exemplary results. Here, on the upper panel killing of the transfected (tricistronic) cell lines against K562 show excellent killing at all tested effector:target ratios. This result is important as the new construct does not affect the killing of the standard K562 line (graphs on the top). Importantly, the newly created CARs kill CD20 and CD33 expressing target cell lines that are otherwise resistant to killing by wildtype NK-92.

In yet further experiments, resilience and function of the erLSP-IL-15 cells will be evaluated. For example, previously frozen erIL-2 CD19 t-haNK and erIL-15 CD19 t-haNK will be thawed and then grows in X-Vivo10 5% without cytokines. Both cell lines are expected to have comparable survival rates and expansion characteristics in the absence of exogenously added cytokines.

In yet further experiments, IL-15 and IL-2 secretion will be measured. Here, it is contemplated that the IL-15 secretion will be equal or outperform IL-2 secretion by at least 5%, or at least 10%, or at least 20%, or at least 40%, or even higher, particularly where the cells also co-express the IL-15 receptor alpha chain. Quantitatively, it is expected that the modified NK=92 cells will secrete at least 100 pg/ml, or at least 150 pg/ml, or at least 200 pg/ml, or even higher IL-15, and that the intracellular quantities (as determined by lysate) will be at least 150 pg/ml, or at least 250 pg/ml, or at least 500 pg/ml, or at least 750 pg/ml, or even higher.

Moreover, it is expected that modified NK-92 cells as described herein will not exhibit clumping or other aggregation during expansion and cultivation. Similarly the cells presented herein (and particularly where the cells express CD16 (preferably high affinity variant) and/or a CAR) will have substantially identical doubling times (i.e., deviation no more than 15%, or nor more than 10%, or no more than 5%) as compared with doubling times of aNK cells or haNK cells using a standard growth assay. Likewise, cells expressing erLSP-IL-15 will typically express functionally active recombinant CAR and/or CD16 in substantially similar quantities (i.e., deviation no more than 15%, or nor more than 10%, or no more than 5%) as compared to haNK cells and t-haNK cells.

Similarly, it is expected that non-specific cytotoxicity against K562 of cells expressing erLSP-IL-15 and recombinant CAR and/or CD16 will be substantially the same as aNK and haNK cells. As already shown above, CAR-mediated cell killing of SUP-B15 by NK-92 cells expressing erLSP-IL-15 and a recombinant CAR is expected as is ADCC-mediated cell killing of SUPB15 CD20+.

From a functional perspective, contemplated modified NK-92 cells presented herein will have comparable or enhanced IFNγ secretion with and without target stimulation (or cytokines panel IFNγ/IL-8/IL-10/chemokines). Moreover, it is expected that contemplated modified NK-92 cells presented herein will have comparable or enhanced expression of flow markers (NKp30, NKp44, NKp46, DNAM-1, NKG2D, NKG2A, NKG2C, CD94, CD96, TIGIT, PD-1, PD-L1, CTLA-4, TIM-3, LAG-3, FasL, TRAIL, T-bet, Eomes, Granzyme B, Perforin)

In still further contemplated methods, RNA seq analysis will be performed to identify the expression pattern, which can be used to track activity and/or presence of modified NK-92 cells within a tumor, among presence and/or activity of other immune competent cells. RNA seq analysis is expected to provide an expression pattern of RNA that is substantially representative of activated NK cells.

As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.). Most preferably, the cells or exosomes are administered via subcutaneous or subdermal injection. However, in other contemplated aspects, administration may also be intravenous injection. Alternatively, or additionally, antigen presenting cells may be isolated or grown from cells of the patient, infected in vitro, and then transfused to the patient. Therefore, it should be appreciated that contemplated systems and methods can be considered a complete drug discovery system (e.g., drug discovery, treatment protocol, validation, etc.) for highly personalized cancer treatment.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the full scope of the present disclosure, and does not pose a limitation on the scope of the invention otherwise claimed. No language in the specification should be construed as indicating any non-claimed element essential to the practice of the claimed invention.

It should be apparent to those skilled in the art that many more modifications besides those already described are possible without departing from the full scope of the concepts disclosed herein. The disclosed subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A genetically modified NK cell, comprising a recombinant nucleic acid that includes a first segment encoding erLSP-IL-15 according to SEQ ID NO:5.

2. The genetically modified NK cell of claim 1, wherein the NK cell is an NK-92 cell.

3. The genetically modified NK cell of claim 1, wherein the recombinant nucleic acid is a DNA.

4. The genetically modified NK cell of claim 3, wherein the recombinant nucleic acid is a linearized plasmid.

5. The genetically modified NK cell of claim 3, wherein the recombinant nucleic acid further comprises a second segment encoding CD16 or a high affinity CD16.

6. The genetically modified NK cell of claim 5, wherein the recombinant nucleic acid further comprises a third segment encoding a chimeric antigen receptor.

7. The genetically modified NK cell of claim 6, wherein the recombinant nucleic acid further comprises a fourth segment encoding a protein that interferes with checkpoint inhibition, a protein that provides immune stimulation, a protein that binds/inhibits a cytokine involved with immune suppression, and/or a IL-15 receptor alpha chain.

8. The genetically modified NK cell of claim 1, wherein the recombinant nucleic acid comprises a promotor having a sufficient strength to drive expression of the erLSP-IL-15 in an amount sufficient to (a) render the modified NK cell independent from exogenous cytokines, and to (b) allow for stimulation/activation of other immune competent cells that are in proximity to the modified NK cell.

9. The genetically modified NK cell of claim 1, further comprising an antibody coupled to the cell via CD 16.

10. A method of modifying an NK cell, comprising: introducing a recombinant nucleic acid into the cell, wherein the recombinant nucleic acid comprises a first segment encoding erLSP-IL-15 according to SEQ ID NO:5.

11. The method of claim 10, wherein the NK cell is an NK-92 cell.

12. The method of claim 10, wherein the recombinant nucleic acid is a DNA.

13. The method of claim 12, wherein the recombinant nucleic acid is a linearized plasmid.

14. The method of claim 12, wherein the recombinant nucleic acid further comprises a second segment encoding CD16 or a high affinity CD16.

15. The method of claim 14, wherein the recombinant nucleic acid further comprises a third segment encoding a chimeric antigen receptor.

16. The method of claim 15, wherein the recombinant nucleic acid further comprises a fourth segment encoding a protein that interferes with checkpoint inhibition, a protein that provides immune stimulation, a protein that binds/inhibits a cytokine involved with immune suppression, and/or a IL-15 receptor alpha chain.

17. The method of claim 10, wherein the recombinant nucleic acid comprises a promotor having a sufficient strength to drive expression of the erLSP-IL-15 in an amount sufficient to (a) render the modified NK cell independent from exogenous cytokines, and to (b) allow for stimulation/activation of other immune competent cells that are in proximity to the modified NK cell.

18. The method of claim 10, further comprising an antibody coupled to the cell via CD16.

19. A pharmaceutical composition comprising a pharmaceutically acceptable carrier in combination with a genetically modified NK cell according to claim 1.

20. The pharmaceutical composition of claim 19, comprising at least $1 \times 10^9$ cells per dosage unit.

* * * * *